United States Patent [19]

Nishida et al.

[11] Patent Number: 5,431,820
[45] Date of Patent: Jul. 11, 1995

[54] METHOD FOR TREATING LIQUID WASTE AFTER PULP BLEACHING

[75] Inventors: Tomoaki Nishida; Yoshimasa Takahara, both of Tsukuba; Kokki Sakai, Munakata; Ryuichiro Kondo; Seon-Ho Lee, both of Fukuoka, all of Japan

[73] Assignee: Kabushiki Kaisha Kobe Seiko Sho, Kobe, Japan

[21] Appl. No.: 70,400

[22] PCT Filed: Sep. 28, 1992

[86] PCT No.: PCT/JP92/01238

§ 371 Date: Jun. 10, 1993

§ 102(e) Date: Jun. 10, 1993

[87] PCT Pub. No.: WO93/07333

PCT Pub. Date: Apr. 15, 1993

[30] Foreign Application Priority Data

Oct. 11, 1991 [JP] Japan .................... 3-290385

[51] Int. Cl.⁶ ................................. C02F 3/34
[52] U.S. Cl. ........................ 210/611; 210/928; 435/278; 435/911
[58] Field of Search ............ 210/610, 611, 928; 435/278, 911

[56] References Cited

U.S. PATENT DOCUMENTS 4,554,075 11/1985 Chang et al. ............... 210/611
4,655,926 4/1987 Chang et al. ............... 210/611
5,091,089 2/1992 Shen et al. .................. 210/611

FOREIGN PATENT DOCUMENTS

| | | |
|---|---|---|
| 51-132655 | 11/1976 | Japan . |
| 52-82776 | 7/1977 | Japan . |
| 54-20189 | 2/1979 | Japan . |
| 3-32996 | 12/1988 | Japan . |
| 3-32997 | 12/1988 | Japan . |
| 1-503125 | 10/1989 | Japan . |
| 2-259180 | 10/1990 | Japan . |
| 3-5878 | 1/1991 | Japan . |
| 3-40887 | 2/1991 | Japan . |
| 3-104993 | 5/1991 | Japan . |
| 3-220388 | 9/1991 | Japan . |
| 8807976 | 10/1988 | WIPO . |

Primary Examiner—Thomas Wyse
Attorney, Agent, or Firm—Oblon, Spivak, McClelland, Maier & Neustadt

[57] ABSTRACT

The liquid waste after pulp bleaching can be treated by using a microorganism having lignin degradation activity and having been pre-cultured in a culture medium supplemented with the liquid waste after pulp bleaching and/or lignin related substances, the cultured products thereof and/or the treated products thereof.

The scarcely degradable colored ingredients and/or chlorinated phenols contained in the liquid waste after pulp bleaching can be decomposed and removed, whereby the efficient treatment of the liquid waste after pulp bleaching can be achieved.

5 Claims, 3 Drawing Sheets

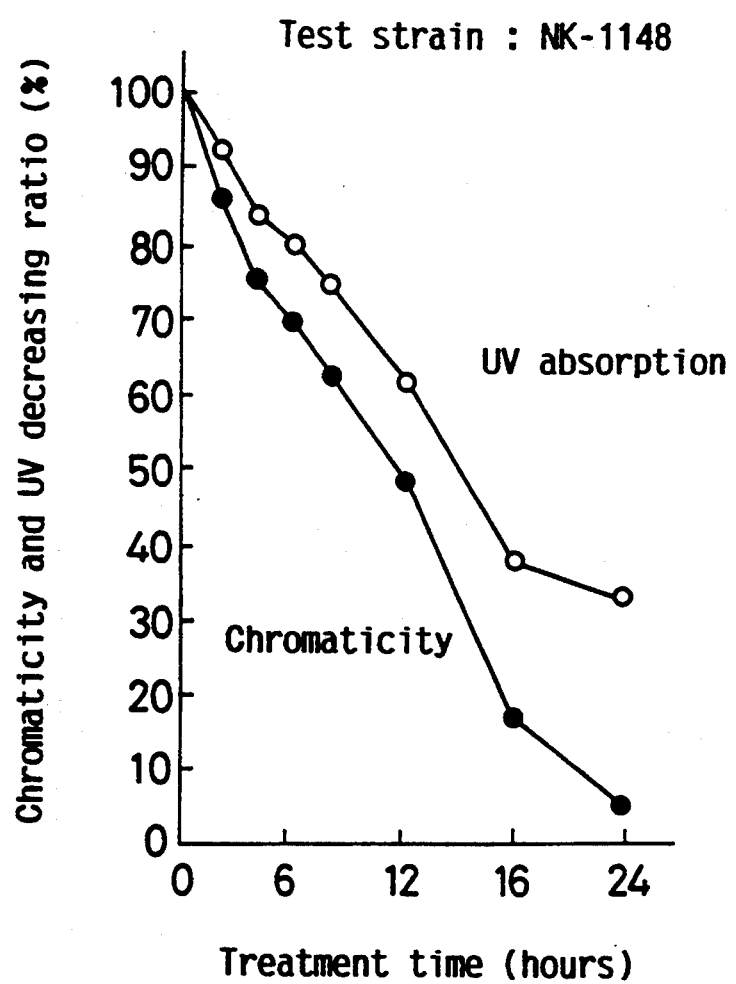

METHOD FOR TREATING LIQUID WASTE AFTER PULP BLEACHING

FIELD OF THE INVENTION

The present invention relates to a method for treating the liquid waste after pulp bleaching. More specifically, the present invention relates to a method for efficiently decomposing and removing scarcely degradable colored ingredients and chlorinated phenols, contained in the liquid waste after pulp bleaching, by using a microorganism having lignin degradation activity which microorganism is cultured in a culture broth supplemented with the liquid waste after pulp bleaching and/or lignin related substances.

Still further, the present invention encompasses a method for efficiently treating the liquid waste after pulp bleaching, by using a lignin degradable microorganism which has a higher lignin degradation activity of high molecular and low molecular lignins and does not cause reverse polymerization, whereby the colored ingredients and chlorinated phenols derived from lignins contained in the liquid waste after pulp bleaching can be decomposed and removed efficiently.

BACKGROUND OF THE INVENTION

Due to the residues of scarcely bleachable lignins, craft pulp as one of principal chemical pulps requires multi-stage bleaching in addition to the bleaching with chlorine chemicals. Because the liquid waste after such bleaching contains chlorine ions, therefore, it is difficult to recover the waste for treatment. Additionally, a report has been published recently that organic chlorine compounds including hazardous dioxines are contained in the liquid waste, which has been drawing attention as one of the sources for environmental pollution. Alternatively, the liquid waste after bleaching is severely colored and contains partially chlorinated lignin degradation products if activated sludge process, a well known process of liquid waste, is applied to the liquid waste. Thus, it is difficult to effectively treat the liquid waste with activated sludge process alone.

Therefore, attempts have been made for the treatment of the liquid waste after pulp bleaching via microorganisms, while focusing on a variety of microorganisms. For example, Japanese Patent Publication No. Hei 3-5878 describes a process of adsorbing or decomposing the chromaticity components in craft pulp liquid waste via the use of Penicillium janthinellum.

Disclosure has been made of examples for decoloring alkali lignins, humic acid and bile acid via the microorganism, but the process is not applied to the liquid waste of craft pulp bleaching so no demonstration of the decoloring effect on the liquid waste of craft pulp bleaching is made therein.

The decoloring of the liquid waste of craft pulp bleaching via Phanerochaete chrysosporium has been reported (Momohara et al., Lumber Research Society, 35(12), 1110(1989)), with the results that no decoloring occurs several days after such fungal treatment and that about two weeks are required for the fungal treatment so as to achieve satisfactory decoloring effect. Thus, the process has not been industrially applied in terms of the long period of treatment and less decoloring effect. Furthermore, a process of decoloring the liquid waste after lumber pulp bleaching has been proposed via Phanerochaete chrysosporium, using a porous carrier (Japanese Patent Laid-open No. Hei 1-503125), but the problem that the process also requires a long period of treatment time with less decoloring effect has remained unsolved.

DISCLOSURE OF THE INVENTION

The present inventors have made investigations so as to achieve a method capable of shortening the period required for such microbial treatment and efficiently decomposing and removing at a higher extent the colored ingredients and chlorinated phenols in the liquid waste after pulp bleaching. Thus, the present invention has achieved the objective.

That is, in accordance with the present invention, enzymes involved in the decomposition of the colored ingredients and chlorinated phenols contained in the liquid waste after pulp bleaching are rapidly produced by using a microorganism having lignin degradation activity and having been pre-cultured in a medium supplemented with the liquid waste after pulp bleaching and/or lignin related substances. The liquid waste can be efficiently treated with the enzymes.

BRIEF DESCRIPTION OF THE DRAWINGS

FIG. 3 is a view depicting the decoloring ratio and the decreasing ratio of the chlorinated phenols when the pre-cultured NK-1148 strain is used the liquid waste after pulp bleaching.

BEST MODE FOR CARRYING OUT THE INVENTION

Figure 1:
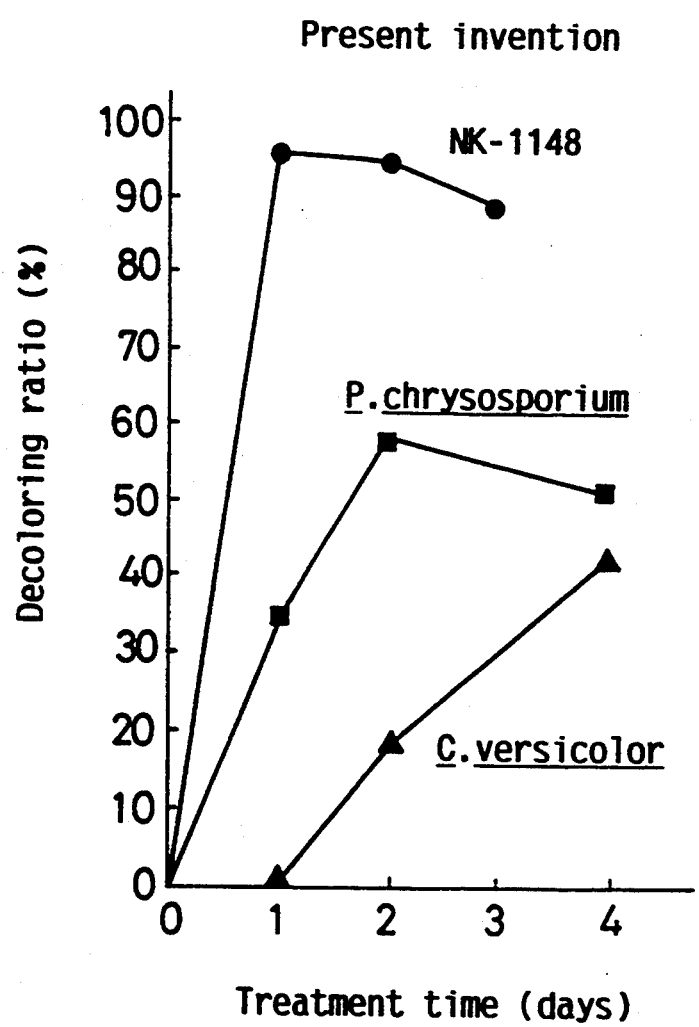
FIG. 1 is a view depicting the decoloring ratio of the liquid waste after pulp bleaching when the pre-cultured fungus is used (the present invention).

As such microorganism, the practice of the invention principally requires a microorganism having lignin degradation activity. In accordance with the present invention, lignin degradation fungi, namely lumber rot fungi such as white rot Basidiomycetes, are widely used.

As such lumber Pot fungi, microorganisms from the following individual genera are illustrated, for example, *Coriolus versicolor* IFO 7043, etc.; *Phanerochaete chrysosporium* ACTT 34541, etc.; *Trametes dickinsii* IFO 6488, etc.; *Polyporus mikadoi* IFO 6517, etc.; *Stereum frustulosum* IFO 4932, etc.; *Ganoderma applanatum* IFO 6499, etc.; *Lenzites betulina* IFO 8714, etc.; *Fomes fomentarius* IFO 30371, etc.; *Porodisculus pendulus* IFO 4967, etc.; *Lentinus edodes* IFO 31336, etc.; *L. lepideus* IFO 7043, etc.; *Serpula lacrymans* IFO 8697, etc.

In accordance with the present invention, the intended objective can be achieved by using the lignin degradable fungi as has been described above. Because the colored ingredients and chlorinated phenols in liquid waste after pulp bleaching are both derived from the lignin degradation products in lumber, further improvement in the processing efficacy can be expected when microorganisms which have a higher degradation activity (anabolic activity) of high molecular and low molecular lignins and of which lignin degradation products, once degraded, do not re-polymerize with each other (reverse polymerization) are used singly or in combination with two or more thereof.

As such highly efficient lignin degradation fungi, for example, NK-1148 strain is illustrated. NK-1148 strain is a fungus isolated by the present inventors, and has characteristic fungal properties as shown in Table 1. The present inventors have submitted the application of the fungal strain (Japanese Patent Publication No. Hei 3-32996).

TABLE 1

| Medium type | Growth state |
| --- | --- |
| Malt extract agar medium | +++ |
| Potato.Glucose agar medium | +++ |
| Czapek agar medium | + |
| Sabouraud agar medium | ++ |
| Synthetic mucor agar medium | ++ |
| YpSs agar medium | +++ |
| Glucose.dry yeast agar medium | +++ |

Note 1. Medium pH: 5.0 (prior to autoclave sterilization)
Note 2. Culture condition: 28° C. for 7 days
Note 3. Growth state
slight: +
moderate: ++
vigorous: +++

1. Physiological, ecological properties (1) pH Range of Growth (Cultured in Potato.Glucose Agar Medium at 28° C. for 4 days)

The fungus grows in about pH 3–9, but does not grow at pH 2 or 10. The optimum pH is around from 4 to 6.

(2) Temperature Range of Growth (Cultured in Potato-Glucose Agar Medium, pH 5 for 4 days)

The fungus grows at about 10° to 45° C., but does not grow at 50° C. The optimum temperature is around from 28° to 37° C., (3) Phenoloxidase Reaction (Cultured at 28° C. for 4 days)

Slightly positive or negative.

(4) Characteristics of Colony (Cultured in Potato.Glucose agar medium, PH 5 at 28° C. for 4 days)

White and felt-like.

The strain NK-1148 not only has higher lignin degradation activity than the fungi of genus Coriolus and the fungi of genus Phanerochaete, these fungi having been well known conventionally as lignin degradation fungi, but also shows more excellent selectivity. The present strain has been approved as a new fungal strain and is designated as strain NK-1148, which is then deposited as FERM BP-1859, in the Patent Microorganism Depository, Fermentation Institute, Agency of Industrial Science and Technology, at 1-3, Higashi 1-chome, Tsukuba-shi, Ibaraki-ken, 305, Japan (Deposition date; May 23, 1987).

As another highly efficient lignin degradation fungus, strain NK-729W is illustrated. The strain NK-729W is a microorganism isolated by the present inventors and is derived from *Porodisculus pendulus*. The present inventors have also submitted the patent application of the fungal strain (Japanese Patent Publication No. Hei 3-32997). The strain NK-729W from Porodisculus pendulus not only has higher lignin degradation activity than conventional fungi, but also shows more excellent selectivity. The present strain has been approved as a new fungal strain of *Porodisculus pendulus* and is designated as a strain NK-729W of *Porodisculus pendulus*, which is then deposited as FERM BP-1860, in the Patent Microorganism Depository, Fermentation Institute, Agency of Industrial Science and Technology, at 1-3, Higashi 1-chome, Tsukuba-shi, Ibarakiken, 305, Japan (Deposition date; May 23, 1987).

It is required to pre-culture the(se) microorganism(s) in a culture medium supplemented with the liquid waste after pulp bleaching and/or lignin related substances prior to the addition thereof to the liquid waste after pulp bleaching to be treated.

As the liquid waste after pulp bleaching to be used in accordance with the present invention, any of the liquid wastes after bleaching generated during routine processes of pulp bleaching, may be used with no specific limitation, but preferably, the alkaline-extracted liquid waste after chlorine bleaching is used. As the lignin related substances, use may be made of low-molecular phenols such as guaiacol etc., kraftlignin, lignosulfonic acid as well as dioxanelignin and ground lignin, etc. which are generated during the process of producing pulp. The(se) may be added to the culture medium at such an appropriate amount, without any limitation, that the properties as the objective may be imparted to the microorganism. This is the case with the culturing period thereof. The(se) may be added of the whole amount thereof once to the culture medium or may be added to the medium in a divided manner. Then, use may be made of a wide variety of culture media where the lignin degradation fungi can grow as the basal medium, but specifically preferable results may be obtained when glucose is used as a carbon source. The same is true with the case where the liquid waste after pulp bleaching is treated by using the(se) fungus (fungi). When glucose is added to the liquid waste, the efficiency of the treatment can further be improved.

The treatment of the liquid waste with the(se) pre-cultured fungus (fungi) can be done by routine methods. The lignin degradable microorganisms described above, the cultured products thereof and/or the treated products thereof may be added to the liquid waste after pulp bleaching as the subject to be treated, followed by treatment at a temperature of about from 20° to 40° C. for a predetermined time. In accordance with the present invention, the cultured products thereof broadly mean the mixture of the fungi generated by culturing a fungus and the culture broth. In accordance with the present invention, further, use may be made of the fungi of wet cake, etc., isolated from fungal culture products, the residue thereof, and the culture broth obtained after totally removing solids. Also, the treated products mean all of those produced by concentrating, drying or diluting what have been described above.

The present invention will now be described in examples. Example 1.

Non-bleached Japanese red pine craft pulp (Kappa value of 40.0) was treated with chlorination (chlorine amount, 9.0% of pulp; reaction temperature, room temperature; pulp concentration, 4%; reaction time, 40 minutes), followed by alkaline extraction (NaOH amount, 6.4% of pulp; reaction temperature, 70° C.; pulp concentration, 10%; reaction time, 60 minutes) to prepare pulp bleached liquid (E1 liquid waste). Then, the waste was adjusted to pH 4.5, which was used as a sample.

NK-1148 strain (FERM BP-1859), *Phanerochaete chrysosporium* (ATCC 34541) and *Coriolus versicolor* (IFO 7043) were cultured in a-culture medium (250 ml) containing 3% glucose, 1% malt extract, 1% peptone and 0.4% yeast extract for two days, followed by addition of 50 ml of the E1 liquid waste described above for another one-day culture. After the culturing, only the fungi were collected and inoculated into 250 ml of the E1 liquid waste containing 0.5% glucose for fungal treatment for 1 to 10 days.

Prior to and after the treatment, the chromaticity (absorbance at 500×465 nm/0.132) and absorbance at 280 nm (when the treatment was done with NK-1148 strain) were measured to calculate the decoloring ratio and the decreasing ratio of chlorinated phenols.

As the control, the fungi each were individually cultured in a culture medium (350 ml) containing 3% glucose, 1% malt extract, 1% peptone, and 0.4% yeast extract for 3 days, and then collected. The same experiment was done with the collected fungi.

Figure 2:
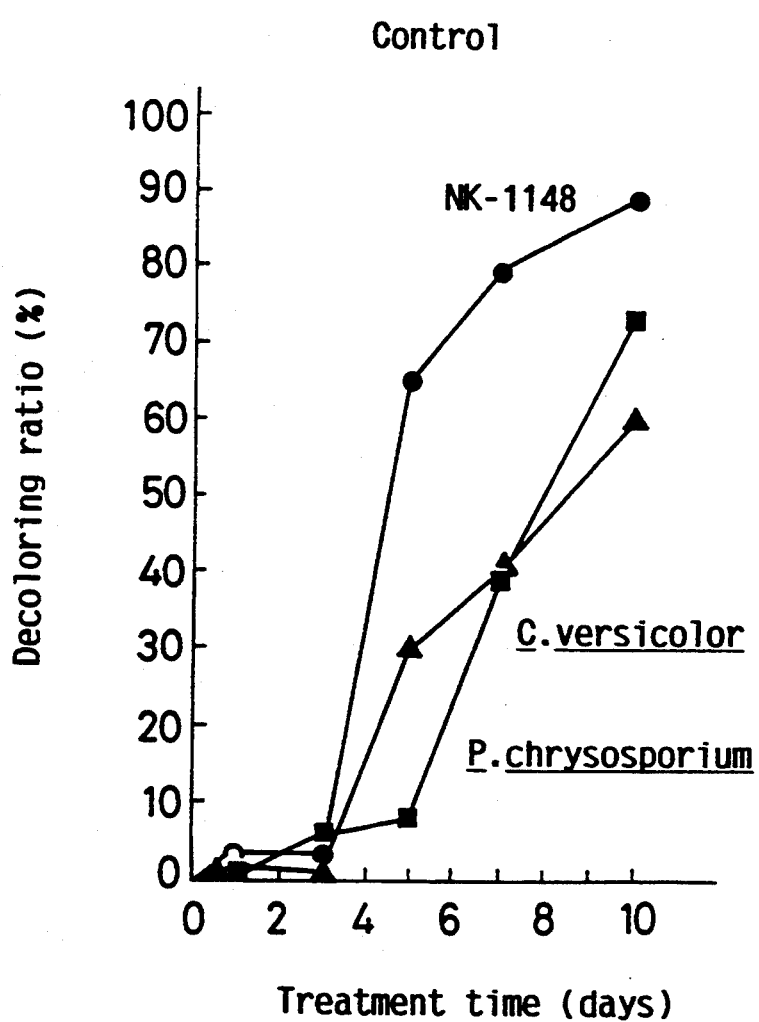
FIG. 2 is a view depicting the decoloring ratio of the liquid waste after pulp bleaching when no pre-cultured fungus is used (control).

The results are shown in FIGS. 1 to 3.

As apparently shown from the results in FIGS. 1 and 2, the individual fungi pre-cultured in the culture medium preliminarily supplemented with the $E_1$ liquid waste (the present invention) showed the following decoloring ratios; NK-1148 strain after the treatment for such a short time as one day showed a higher decoloring ratio of 95%; *P. chrysosdorium* after the treatment for two days showed a decoloring ratio of 58%; *C. versicolor* after the treatment for 4 days showed a decoloring ratio of 42%. It has been demonstrated that the use of the pre-cultured fungi can achieve efficient decoloring of $E_1$ liquid waste. It has been demonstrated, on the contrary, that the use of non-pre-cultured fungi (control) requires a long period of time for treating the liquid waste after pulp bleaching with less efficiency of the treatment.

The present inventors have showed in Japanese Patent Application No. Hei 3-69421, submitted on Mar. 11, 1991 that the NK-1148 strain was characterized in excellent water solubilization of high molecular lignins and the degradation into lower molecular products, and was characterized in that the strain could use high molecular lignins without involving the polymerization of the degraded lignins of low molecular weights. The NK-1148 strain most efficiently decolors $E_1$ liquid waste, and such characteristic properties thereof are found to be significant for the decoloring of the liquid waste after pulp bleaching.

FIG. 3 indicates that the removal of the colored ingredients involves the removal of the chlorinated phenols, which demonstrates the effectiveness of the present invention.

INDUSTRIAL APPLICABILITY

In accordance with the present invention, the liquid waste after pulp bleaching which conventionally has hardly been treated industrially can be treated at a higher efficiency for a very short period. Thus, the present invention is very useful as a pollution prevention technique.

What is claimed is:

1. A method for treating a liquid waste generated after a pulp bleaching step Of a pulp bleaching process, comprising decomposing and removing scarcely degradable colored ingredients and chlorinated phenols contained in the liquid waste, by using a microorganism having lignin degradation activity and having been pre-cultured in a culture medium supplemented with the liquid waste and lignin related substances, wherein said microorganism is selected from the group consisting of NK-1148 Strain and NK-729W strain.

2. A method for treating a liquid waste generated after a pulp bleaching Step of a pulp bleaching process, comprising preculturing a microorganism selected from the group consisting of NK-1158 strain and NK-729W strain, having lignin degradation activity, in a culture medium supplemented with the liquid waste, and decomposing scarcely-degradable colored ingredients or chlorinated phenols or both contained in the liquid waste by using the microorganism.

3. A method for treating a liquid waste generated after a pulp bleaching step of a pulp bleaching process, comprising preculturing a microorganism selected from the group consisting of NK-1158 strain and NK-729W strain, having lignin degradation activity, in a culture medium supplemented with lignin related substances, and decomposing scarcely-degradable colored ingredients or chlorinated phenols or both in the liquid waste by using the microorganism.

4. A method for treating a liquid waste generated after a pulp bleaching step of a pulp bleaching process, comprising preculturing a microorganism having lignin degradation activity in a culture medium and decomposing scarcely-degradable colored ingredients contained in the liquid waste by using the microorganism, wherein said microorganism is NK-1148 strain and the culture medium is supplemented with the liquid waste and lignin related substances.

5. A method for treating a liquid waste generated after a pulp bleaching step of a pulp bleaching process, comprising preculturing a microorganism having lignin degradation activity in a culture medium and decomposing scarcely-degradable colored ingredients contained in the liquid waste by using the microorganism, wherein said microorganism is NK-729W strain and the culture medium is supplemented with the liquid waste and lignin related substances.

* * * * *

UNITED STATES PATENT AND TRADEMARK OFFICE
CERTIFICATE OF CORRECTION

PATENT NO. : 5,431,820
DATED : July 11, 1995
INVENTOR(S) : Tomoaki Nishida et al.

It is certified that error appears in the above-indentified patent and that said Letters Patent is hereby corrected as shown below:

Column 4: line 63, "a-culture"
    should read    --a culture--;
Column 5: lines 16, 25 and 38, "$E_1$"
    should read    --E1--;
Column 6: line 5, "Of"
    should read    --of--;
    line 13, "Strain" (first instance)
    should read    --strain--;
    line 15, "Step"
    should read    --step--;
    line 17, "NK-1158"
    should read    --NK-1148;
    line 26, "NK-1158"
    should read    --NK-1148--.

Signed and Sealed this

Fourteenth Day of January, 1997

Attest:

BRUCE LEHMAN

*Attesting Officer*      Commissioner of Patents and Trademarks